United States Patent
Maunz et al.

(10) Patent No.: US 12,293,515 B2
(45) Date of Patent: May 6, 2025

(54) CHOROIDAL NEOVASCULARIZATION CLASSIFICATION

(71) Applicant: Hoffmann-La Roche Inc., Little Falls, NJ (US)

(72) Inventors: Andreas Maunz, Basel (CH); Fethallah Benmansour, Basel (CH); Yun Li, Basel (CH); Thomas Felix Albrecht, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 375 days.

(21) Appl. No.: 17/780,925

(22) PCT Filed: Nov. 18, 2020

(86) PCT No.: PCT/EP2020/082579
§ 371 (c)(1),
(2) Date: May 27, 2022

(87) PCT Pub. No.: WO2021/110417
PCT Pub. Date: Jun. 10, 2021

(65) Prior Publication Data
US 2022/0414871 A1    Dec. 29, 2022

(30) Foreign Application Priority Data
Dec. 5, 2019 (EP) .................................. 19213846

(51) Int. Cl.
*G06T 7/11* (2017.01)
*G06T 7/00* (2017.01)
(Continued)

(52) U.S. Cl.
CPC .............. *G06T 7/0012* (2013.01); *G06T 7/11* (2017.01); *G06T 7/60* (2013.01); *G16H 50/20* (2018.01);
(Continued)

(58) Field of Classification Search
CPC ......... G06T 7/0012; G06T 2207/30096; G06T 2207/30041; G06T 7/11; G06T 7/60;
(Continued)

(56) References Cited

U.S. PATENT DOCUMENTS 10,925,480 B2 * 2/2021 Huang ................ A61B 3/0025
2016/0135683 A1 5/2016 Yasuno et al.
(Continued)

FOREIGN PATENT DOCUMENTS

CN 105488350 A 4/2016
CN 106943124 A 7/2017
(Continued)

OTHER PUBLICATIONS

Roy et al. "ReLayNet: retinal layer and fluid segmentation of macular optical coherence tomography using fully convolutional networks"; Biomedical optics express 8.8: 3627-3642 (Year: 2017).*
(Continued)

*Primary Examiner* — Sumati Lefkowitz
*Assistant Examiner* — Michael Adam Shariff
(74) *Attorney, Agent, or Firm* — The Webb Law Firm

(57) ABSTRACT

A method for identifying a type of choroidal neovascularization in a retina of a human eye is disclosed, the method comprising receiving, in a processor, optical coherence tomography data of the eye; generating, in the processor, volume segments of the eye using the optical coherence tomography data and a neural network; and identifying, in the processor, the type of choroidal neovascularization in the eye, using the volume segments, the type of choroidal neovascularization comprising one or more of the following: classic choroidal neovascularization and occult choroidal neovascularization.

21 Claims, 7 Drawing Sheets

(51) Int. Cl.
*G06T 7/60* (2017.01)
*G16H 50/20* (2018.01)
*A61B 3/10* (2006.01)

(52) U.S. Cl.
CPC ..... *A61B 3/102* (2013.01); *G06T 2207/10101* (2013.01); *G06T 2207/20081* (2013.01); *G06T 2207/20084* (2013.01); *G06T 2207/30041* (2013.01); *G06T 2207/30096* (2013.01)

(58) Field of Classification Search
CPC . G06T 2207/10101; G06T 2207/20081; G06T 2207/20084; G16H 50/20; A61B 3/102
See application file for complete search history.

(56) References Cited

U.S. PATENT DOCUMENTS

| | | | |
|---|---|---|---|
| 2016/0278627 A1 | 9/2016 | Huang et al. | |
| 2018/0047159 A1 | 2/2018 | Schlegl et al. | |
| 2018/0260952 A1 | 9/2018 | Bagherinia et al. | |
| 2018/0344147 A1 | 12/2018 | Huang et al. | |
| 2020/0293952 A1* | 9/2020 | Siddiqui | G06F 18/24323 |
| 2022/0207729 A1* | 6/2022 | Boyd | G06V 10/774 |

FOREIGN PATENT DOCUMENTS

| | | |
|---|---|---|
| CN | 108885687 A | 11/2018 |
| CN | 109730633 A | 5/2019 |
| JP | 20195319 A | 1/2019 |
| JP | 2019192215 A | 10/2019 |
| WO | 2016154485 A1 | 9/2016 |

OTHER PUBLICATIONS

Guan et al., "Fully Automated Detection and Quantification of Multiple Retinal Lesions in OCT Volumes Based on Deep Learning and Improved DRLSE", Proceedings of SPIE, 2019, pp. 1094933-1-1094933-7, vol. 10949.

Guha Roy et al., "ReLayNet: Retinal Layer and Fluid Segmentation of Macular Optical Coherence Tomography using Fully Convolutional Network", Arxiv.org, 2017, pp. 1-24.

Guha Roy et al., "RelayNet: Retinal Layer and Fluid Segmentation of Macular Optical Coherence Tomography using Fully Convolutional Network", Biomed Optics Express, 2017, pp. 3627-3642, vol. 8:8.

* cited by examiner

CHOROIDAL NEOVASCULARIZATION CLASSIFICATION

CROSS-REFERENCE TO RELATED APPLICATIONS

This application is the United States national phase of International Application No. PCT/EP2020/082579 filed Nov. 18, 2020, and claims priority to European Patent Application No. 19213846.9 filed Dec. 5, 2019, the disclosures of each of which are hereby incorporated by reference in their entireties.

FIELD OF THE INVENTION

The present invention relates to a method and device for identifying a type of choroidal neovascularization in a human eye. Specifically, the present invention relates to a computer-implemented method, a computer, and a computer program product for identifying a type of choroidal neovascularization in a human eye.

BACKGROUND OF THE INVENTION

The eye contains many different types of tissues and fluids. The rear (posterior portion) of the eye can be roughly divided into the following layers: the neurosensory retina which comprises 2nd order and 3rd order neurons and photo receptors, the retinal pigment epithelium layer which is a pigmented cell layer just beyond the neurosensory retina which nourishes these retinal visual cells, and the choroid layer, which is the vascular layer of the eye and contains blood vessels and connective tissue. These layers can of course be further subdivided. Choroidal neovascularization (CNV) is the creation of new blood vessels in the choroid layer. These new blood vessels can cause lesions. These lesions can contain components other than blood vessels, such as fibrosed tissue, hemorrhage, pigmentation, or other features that may obscure the boundaries of the CNV.

Choroidal neovascularization can be divided into two types: classic and occult. Classic CNV lesions typically penetrate the retinal pigment epithelium (RPE), and are therefore located in front (anterior) of the RPE, whereas occult lesions are sub-RPE. Classic CNVs are considerably less frequent than occult or mixed type forms (mixed type is where both classic and occult lesions are present). The common definition of CNV type in use today is based on the Macular Photocoagulation Study (MPS). To determine which type of choroidal neovascularization is present, invasive fluorescein angiography (FA) is used, in which a fluorescent dye is added into the circulation of the patient, either intravenously in intravenous fluorescein angiography, or orally in oral fluorescein angiography. The retina is then illuminated with blue light, and an angiogram is obtained by photographing the fluorescent green light that is emitted by the dye. A classic CNV is defined as a clearly visible and well-demarcated bright hyperfluorescence in the early phase of the angiogram, with increasing leakage in the late phase of angiography with blurring of the margin of hyperfluorescence (leakage). Occult CNV is determined by an irregular elevation of the RPE with stippled or granular hyperfluorescence after 1-2 minutes. The boundary may or may not show leakage as time passes. Fluorescein angiography carries risks, as the use of fluorescein dye can cause adverse reactions, including nausea, vomiting, hives, acute hypotension, and, more seriously, anaphylaxis and related anaphylactoid reactions, causing cardiac arrest.

Classic CNV can occur in exudative age-related macular degeneration (ARMD), but also secondary to other conditions, such as ocular histoplasmosis syndrome, pathologic myopia, choroidal rupture, angioid streaks, or idiopathic causes.

Optical coherence tomography (OCT) offers a method for the creating an optical cross-section of the eye which is non-invasive and high-resolution. Currently, OCT is used to evaluate patients with ARMD. The imaging helps doctors and clinicians evaluate for tomographic sequelae of neovascular membranes, as well as monitor for treatment responses. The type of light used in OCT allows it to penetrate deep into tissue and examine tissue and fluid layers even with a high reflectivity. In OCT, typically many one-dimensional scans (A-scans) are performed at several depths in the retina. These A-scans can then be combined to form two-dimensional cross-sections of the eye in so-called B-scans. The B-scans can then be combined to form a three-dimensional image of the eye, also called a C-scan. With advanced OCT methods such as spectral domain OCT (SD-OCT), the acquisition time of OCT images has been shortened, and along with techniques to track and compensate for the movement of the eye and blinking, the accuracy of the OCT images has also improved.

WO 2016/154485 describes methods of detecting, visualizing, and measuring the extent of retinal neovascularization. The methods involve receiving a set of cross-sectional angiograms, segmenting the set of cross sectional angiograms into layers, and generating an en face inner retina angiogram and an en face vitreous angiogram.

Abhijit Guha Roy, et al., "ReLayNet: retinal layer and fluid segmentation of macular optical coherence tomography using fully convolutional networks," Biomed. Opt. Express 8, 3627-3642 (2017), discloses a method for segmenting 2D retinal layers and fluids in retinal OCT data. The disclosed method uses a neural network to assign each pixel of an OCT B-scan to one of ten classes.

SUMMARY OF THE INVENTION

It is an object of this invention to provide a technical solution for identifying a type of choroidal neovascularization in a human eye. Disclosed are a computer-implemented method, a computer, and a computer program product for identifying a type of choroidal neovascularization in a human eye.

According to some non-limiting embodiments, these objects are achieved through the features of the independent claims. In addition, further advantageous non-limiting embodiments follow from the dependent claims and the description.

According to some non-limiting embodiments, the above-mentioned objects are particularly achieved by a computer-implemented method for identifying a type of choroidal neovascularization in a human eye, the method comprising the steps of receiving, in a processor of a computer, optical coherence tomography data of the eye, in particular of the retinal area of the eye. In another step, volume segments of the human eye are generated in the processor using the optical coherence tomography data and a neural network. In another step, the processor, using the volume segments, identifies the type of choroidal neovascularization in the eye. The type of choroidal neovascularization comprises one or more of the following: classic choroidal neovascularization and occult choroidal neovascularization.

In some non-limiting embodiments, generating the volume segments comprises the processor detecting tissue layer segments and fluidic segments.

In some non-limiting embodiments, generating the volume segments comprises detecting one or more of the following types of tissue layer segments: internal limiting membrane segments, retinal pigment epithelium segments, and Bruch's membrane segments.

In some non-limiting embodiments, generating the volume segments comprises detecting one or more of the following types of fluidic segments: intraretinal fluid segments, subretinal fluid segments, subretinal hyperreflective material segments, central subfield segments, and pigment epithelial detachment segments.

In some non-limiting embodiments, identifying the type of choroidal neovascularization comprises weighting the following types of fluidic segments highest: subretinal hyperreflective material segments, subretinal fluid segments and pigment epithelial detachment segments.

In some non-limiting embodiments, identifying the type of choroidal neovascularization comprises identifying lesions in the eye.

In some non-limiting embodiments, the method further comprises calculating one or more of the following geometric parameters: heights of the volume segments, widths of the volume segments, and distances between the volume segments; and identifying the type of choroidal neovascularization further comprises using the geometric parameters.

In some non-limiting embodiments, identifying the type of choroidal neovascularization comprises using a decision tree.

In some non-limiting embodiments, generating the volume segments comprises training the neural network using machine learning and a neural network training dataset of optical coherence tomography data of a large number of eyes.

In some non-limiting embodiments, identifying the type of choroidal neovascularization comprises optimizing the decision tree using a decision tree training dataset of optical coherence tomography data of a large number of eyes and a gradient boosting algorithm.

In some non-limiting embodiments, identifying the type of choroidal neovascularization comprises optimizing the decision tree using a CatBoost algorithm.

In some non-limiting embodiments, generating the volume segments using the neural network comprises using a convolutional neural network.

In some non-limiting embodiments, generating the volume segments using the neural network comprises using a U-Net and/or a residual neural network (ResNet).

In some non-limiting embodiments, the method further comprises extracting, in the processor, A-scans and/or B-scans from the received optical coherence tomography data, and generating the volume segments further comprises generating area segments using the A-scans and/or B-scans and the neural network.

In some non-limiting embodiments, receiving optical coherence tomography data comprises receiving one or more of the following: time domain optical coherence tomography data, spectral domain optical coherence tomography data, ultrahigh speed swept source optical coherence tomography data, ultrahigh resolution optical coherence tomography data, polarization sensitive optical coherence tomography data, and adaptive optics optical coherence tomography data.

In some non-limiting embodiments, identifying the type of choroidal neovascularization further comprises identifying whether the eye has classic choroidal neovascularization, occult choroidal neovascularization, classic and occult choroidal neovascularization, or no choroidal neovascularization.

In addition to the computer-implemented method for identifying a type of choroidal neovascularization in a human eye, also disclosed is a computer for identifying a type of choroidal neovascularization in a human eye, the computer comprising a processor. The processor is configured to receive optical coherence tomography data of the eye, in particular of the retina of the eye. The processor is configured to generate volume segments of the human eye using the optical coherence tomography data and a neural network, and identify the type of choroidal neovascularization in the eye, using the volume segments. The type of choroidal neovascularization comprises one or more of the following: classic choroidal neovascularization and occult choroidal neovascularization.

In some non-limiting embodiments, the processor is configured to generate the volume segments by detecting one or more tissue layer segments and/or fluidic segments.

In some non-limiting embodiments, the processor is configured to generate the volume segments by detecting one or more of the following types of tissue layer segments: internal limiting membrane segments, retinal pigment epithelium segments, and Bruch's membrane segments.

In some non-limiting embodiments, the processor is configured to generate the volume segments by detecting one or more of the following types of fluidic segments: intraretinal fluid segments, subretinal fluid segments, subretinal hyperreflective material segments, central subfield segments, and pigment epithelial detachment segments.

In some non-limiting embodiments, the processor is configured to identify the type of choroidal neovascularization by weighting the following types of fluidic segments highest: subretinal hyperreflective material segments, subretinal fluid segments and pigment epithelial detachment segments.

In some non-limiting embodiments, the processor is configured to identify the type of choroidal neovascularization by identifying lesions in the eye.

In some non-limiting embodiments, the processor is further configured to calculate geometric data comprising one or more of the following geometric parameters: heights of the volume segments, widths of the volume segments, and distances between the volume segments; and to identify the type of choroidal neovascularization by using the geometric parameters.

In some non-limiting embodiments, the processor is configured to identify the type of choroidal neovascularization using a decision tree.

In some non-limiting embodiments, the processor is configured to generate the volume segments by training the neural network using machine learning and a neural network training dataset of optical coherence tomography data of a large number of eyes.

In some non-limiting embodiments, the processor is configured to identify the type of choroidal neovascularization by optimizing the decision tree using a decision tree training dataset of optical coherence tomography data of a large number of eyes and a gradient boosting algorithm.

In some non-limiting embodiments, the processor is configured to identify the type of choroidal neovascularization by optimizing the decision tree using a CatBoost algorithm.

In some non-limiting embodiments, the processor is configured to generate the volume segments using the neural network by using a convolutional neural network.

In some non-limiting embodiments, the processor is configured to generate the volume segments using the neural network by using one or more of the following: a U-Net and a ResNet.

In some non-limiting embodiments, the processor is configured to extract A-scans and/or B-scans from the received optical coherence tomography data and generate the volume segments by generating area segments using the A-scans and/or B-scans and the neural network.

In some non-limiting embodiments, the processor is configured to receive one or more of the following types of optical coherence tomography data: time domain optical coherence tomography data, spectral domain optical coherence tomography data, ultrahigh speed swept source optical coherence tomography data, ultrahigh resolution optical coherence tomography data, polarization sensitive optical coherence tomography data, and adaptive optics optical coherence tomography data.

In some non-limiting embodiments, the processor is configured to identify the type of choroidal neovascularization by identifying whether the eye has classic choroidal neovascularization, occult choroidal neovascularization, classic and occult choroidal neovascularization, or no choroidal neovascularization.

In addition to the computer-implemented method for identifying a type of choroidal neovascularization in a human eye and a computer comprising a processor configured to identify a type of choroidal neovascularization in a human eye, also disclosed is a computer program product for identifying a type of choroidal neovascularization in a human eye and a computer. The computer program product comprises a non-transitory computer-readable medium having stored thereon computer program code configured to control a processor of a computer such that the computer performs the steps of receiving, in the processor, optical coherence tomography data of the eye, in particular of the retina of the eye. In another step, volume segments of the human eye using the optical coherence tomography data and a neural network are generated in the processor. In another step, the processor, using the volume segments, identifies the type of choroidal neovascularization in the eye. The type of choroidal neovascularization comprises one or more of the following: classic choroidal neovascularization and occult choroidal neovascularization.

BRIEF DESCRIPTION OF THE DRAWINGS

The present invention will be explained in more detail, by way of example, with reference to the drawings in which.

DETAILED DESCRIPTION OF THE PREFERRED EMBODIMENTS

Figure 1:
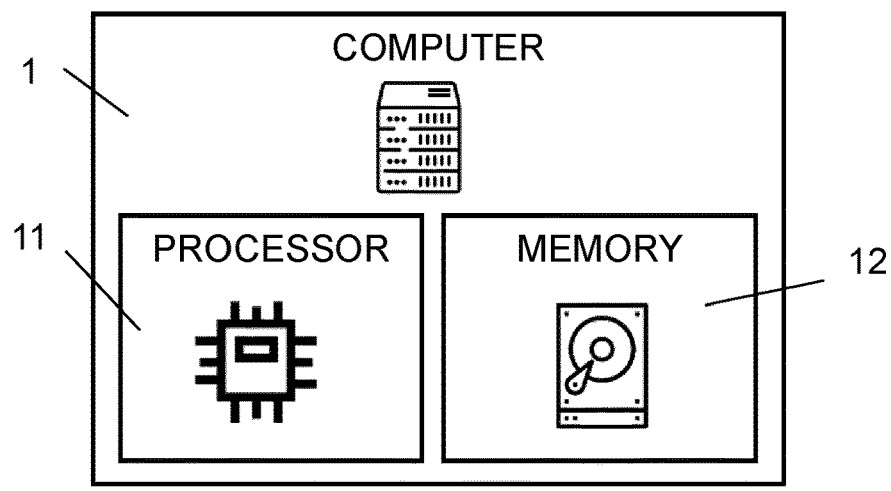
FIG. 1: shows a block diagram illustrating schematically a computer comprising a processor and a memory.

In FIG. 1, reference numeral 1 refers to a computer comprising one or more processors 11. The computer 1 can further include various components, such as a memory 12, a communication interface, and/or a user interface. The components of the computer 1 can be connected to each other via a data connection mechanism, such that they can transmit and/or receive data.

The term data connection mechanism means a mechanism that facilitates data communication between two components, devices, systems, or other entities. The data connection mechanism can be wired, such as a cable or system bus. The data connection mechanism can also include wireless communication. The data connection mechanism can also include communication via networks, such as local area networks, mobile radio networks, and/or the Internet. The Internet can include, depending on the implementation, intermediary networks.

The processor 11 may comprise a system on a chip (SoC), a central processing unit (CPU), and/or other more specific processing units such as a graphical processing unit (GPU), application specific integrated circuits (ASICs), reprogrammable processing units such as field programmable gate arrays (FPGAs), as well as processing units specifically configured to accelerate certain applications, such as AI (Artificial Intelligence) Accelerators for accelerating neural network and/or machine learning processes.

The memory 12 comprises one or more volatile and or non-volatile storage components. The storage components may be removable and/or non-removable, and can also be integrated, in whole or in part with the processor 11. Examples of storage components include RAM (Random Access Memory), flash memory, hard disks, data memory, and/or other data stores. The memory 12 comprises a non-transitory computer-readable medium having stored thereon computer program code configured to control the processor 11, such that the computer 1 performs one or more steps and/or functions as described herein. Depending on the embodiment, the computer program code is compiled or non-compiled program logic and/or machine code. As such, the computer 1 is configured to perform one or more steps and/or functions. The computer program code defines and/or is part of a discrete software application. One skilled in the art will understand that the computer program code can also be distributed across a plurality of software applications. In some non-limiting embodiments, the computer program code further provides interfaces, such as APIs, such that functionality and/or data of the computer 1 can be accessed remotely, such as via a client application or via a web browser.

In some non-limiting embodiments, the computer 1 is implemented as a server computer which is accessible via network by one or more client computing devices.

Figure 2:
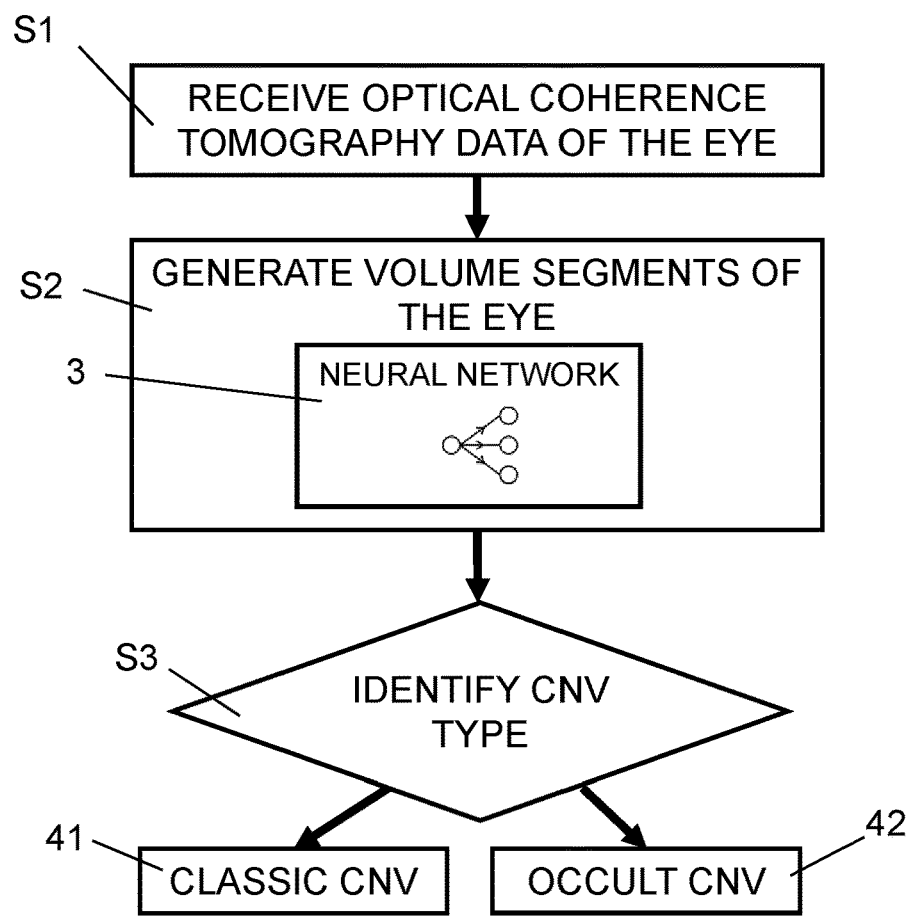
FIG. 2: shows a flow diagram illustrating a sequence of steps for identifying a type of choroidal neovascularization in the eye.

FIG. 2 shows a flow diagram illustrating a sequence of steps for carrying out the described methods, according to non-limiting embodiments.

In step S1, the computer 1 receives optical coherence tomography (OCT) data of an eye. In particular, the processor 11, using the data connection mechanism, receives the OCT data of a human eye. In a prior step, the OCT data is generated by an OCT system using light interferometry as is known to the person skilled in the art.

In some non-limiting embodiments, OCT data comprises one or more of the following: time domain optical coherence tomography (TD-OCT) data, spectral domain optical coherence tomography data (SD-OCT), ultrahigh speed swept source optical coherence tomography data, ultrahigh resolution optical coherence tomography data, polarization sensitive optical coherence tomography data, and adaptive optics optical coherence tomography data. In a preferred embodiment, SD-OCT data is used.

The OCT data is stored either in a memory of a separate server or stored directly on the computer 1 in the memory 12. In cases where the OCT data is stored in the memory 12, the processor 11 can directly retrieve the OCT data from the memory 12. In cases where the OCT data is stored on the memory of the separate server, the processor 11 must first retrieve the OCT data. The processor 11 generates a three-dimensional image or model of the eye, or part of the eye, using the OCT data. In particular, the processor 11 generates a three-dimensional image or model of a section of the retina of the eye.

In step S2, volume segments 2 are generated by the processor 11 using a neural network 3 which has as an input the OCT data. The neural network 3 is stored in the memory 12. The processor 11, using the neural network 3, outputs volume segments 2, which volume segments 2 are regions of space in the eye, in particular of the retinal area. The volume segments 2 are regions of space within the three-dimensional image or model of the section of the retina of the eye generated by the processor 11 using the OCT data. In particular, the volume segments 2 are regions of space which have a substantial extension in all three dimensions, such that the volume segments 2 do not correspond to two-dimensional slices of mere nominal thickness. In some non-limiting embodiments, a given tissue layer or fluid layer of the retinal area of the eye is represented in a single volume segment 2, such that a surjective function exists between the tissue layers and fluid layers, and the volume segments 2. Preferably, contiguous volume segments 2, i.e., volume segments 2 next to each other, do not have adjacent tissue layers or fluid layers of the same type.

In some non-limiting embodiments, each volume segment 2 corresponds to one particular type of tissue or fluid of the eye, in particular tissue layers or fluid layers of the retinal area, and each tissue layer or fluid layer corresponds to one particular volume segment 2, such that a bijective function exists between volume segments 2 and layers of the eye, i.e. tissue layers and fluid layers.

In some non-limiting embodiments, the volume segments 2 are labelled with features. The features comprise one or more of a plurality of types of volume segments 2, as is explained below in the description of FIG. 3.

In some non-limiting embodiments, the neural network 3 uses convolutional layers. Preferably, the neural network 3 is adapted to efficiently handle three-dimensional input data. Preferably, the neural network 3 comprises a U-Net and/or a ResNet architecture, as these two types of neural networks 3 can be used and/or adapted to achieve good results in generating volume segments 2 in three-dimensional data.

The neural network 3 is trained to generate volume segments 2 using machine learning and a neural network training dataset of OCT data of a large number of eyes. This neural network training dataset comprises defined volume segments 2 of OCT data, such that the neural network 3 can be trained using known methods to generate volume segments 2 of OCT data of previously unseen eyes. The neural network training dataset comprises eyes (defined by respective eye data) which have classic choroidal neovascularization 41 and occult choroidal neovascularization 42. In some non-limiting embodiments, the neural network training dataset further comprises eyes (defined by respective eye data) which have no choroidal neovascularization (healthy eyes).

In some non-limiting embodiments, the volume segments 2 of the neural network training dataset are further annotated with features comprising a type and descriptors, and training the neural network 3 comprises training the neural network 3 to label the generated volume segments 2 with one or more features. The trained neural network 2 therefore assigns features to each generated volume segment 2. The descriptors may comprise geometric parameters 6 which relate to the volume segments 2, as is explained in more detail in the description of FIG. 4.

Each volume segment 2 is a three-dimensional image, model, or representation defined by a set of voxels of the three-dimensional OCT data which belong to that particular volume segment 2. Alternatively, the volume segments 2 can be defined by meshes, such as polygon meshes. The volume segments 2 can overlap each other, or they can also be non-overlapping. As described above, the volume segments 2 may be labelled with features.

In step S3, the processor 11 uses the generated volume segments 2 to identify a type of choroidal neovascularization 40 of the eye. The types of neovascularization identified comprise classic choroidal neovascularization 41 and occult choroidal neovascularization 42. The processor 11 uses one or more models, algorithms, and/or functions to identify the type of choroidal neovascularization 40 present in the retina of the eye.

Using volume segments 2 to identify the type of neovascularization, rather than a plurality of 2D slices, for example, allows the processor 11 to improve the performance of identifying the type of choroidal neovascularization. More specifically, using volume segments 2 enables the processor 11 to identify the type of choroidal neovascularization with greater specificity and sensitivity. This is because the retina of the eye is a three dimensional physical structure, and therefore a three dimensional representation is naturally more suitable. In particular, three dimensional properties of the retinal area of the eye and the various tissue layers and fluidic layers, such as geometric parameters of a given tissue layer or fluidic layer, or geometric relationships between a given tissue layer or a given fluidic layer and other tissue layers or fluidic layers, are more directly represented in a set of volume segments 2 and their associated features. This more direct and natural representation of a given fluidic layer or tissue layer as a single volume segment 2, rather than as a set of regions of 2D space in a set of 2D scans, is exemplified in that this allows for a simple and less complex function to exist (in particular a surjective or bijective function) between volume segments 2 (representation) and fluidic layers and tissue layers (reality). In particular, fewer volume segments 2 are required to represent the retinal area of the eye, than 2D area segments of a set of 2D scans would be required.

In some non-limiting embodiments, the processor 11 is further configured to identify the absence of choroidal neovascularization 40 using one or more models, algorithms, and/or functions, and thus to determine whether or not the eye is healthy. In particular, the processor 11 is configured to identify eyes which are healthy, eyes which have classic choroidal neovascularization 41, and eyes which have occult choroidal neovascularization 42.

In some non-limiting embodiments, the processor 11 uses a nearest neighbor algorithm to identify a type of choroidal neovascularization 40 of the eye in question. The nearest neighbor algorithm is a supervised classification algorithm which uses a labelled classification training dataset. The classification training dataset comprises volume segments 2 of a large number of eyes with a known type of choroidal neovascularization 40. The nearest neighbor algorithm checks which eye belonging to the classification training dataset has volume segments 2 most closely corresponding to the volume segments 2 of the eye in question and assigns the type of choroidal neovascularization 40 of the eye belonging to the classification training dataset to the eye in question.

In some non-limiting embodiments, the processor 11 uses logistic regression to identify a type of choroidal neovascularization 40 of the eye in question. Logistic regression is a statistical model for analyzing a dataset comprising one or more independent variables, where the output is a dichotomous variable. The processor 11 uses logistic regression and a labelled classification training dataset, comprising volume segments 2 of a large number of eyes with a known type of choroidal neovascularization 40, to generate a model which can identify the type of choroidal neovascularization 40 of the eye in question.

In some non-limiting embodiments, the processor 11 uses a support vector machine to identify a type of choroidal neovascularization 40 present in the eye in question. The support vector machine uses a classification training dataset, comprising volume segments 2 of a large number of eyes with a known type of choroidal neovascularization 40, to generate an optimal hyperplane which is used by the processor 11 to identify which type of choroidal neovascularization 40 is present in the eye in question.

In some non-limiting embodiments, the processor 11 uses a separate neural network to identify the type of choroidal neovascularization 40 in the eye. The neural network uses a classification training dataset, comprising volume segments 2 of a large number of eyes with a known type of choroidal neovascularization 40, to optimize a set of internal weights and biases which are then used by the processor 11 to identify which type of choroidal neovascularization 40 is present in the eye in question.

Figure 6:
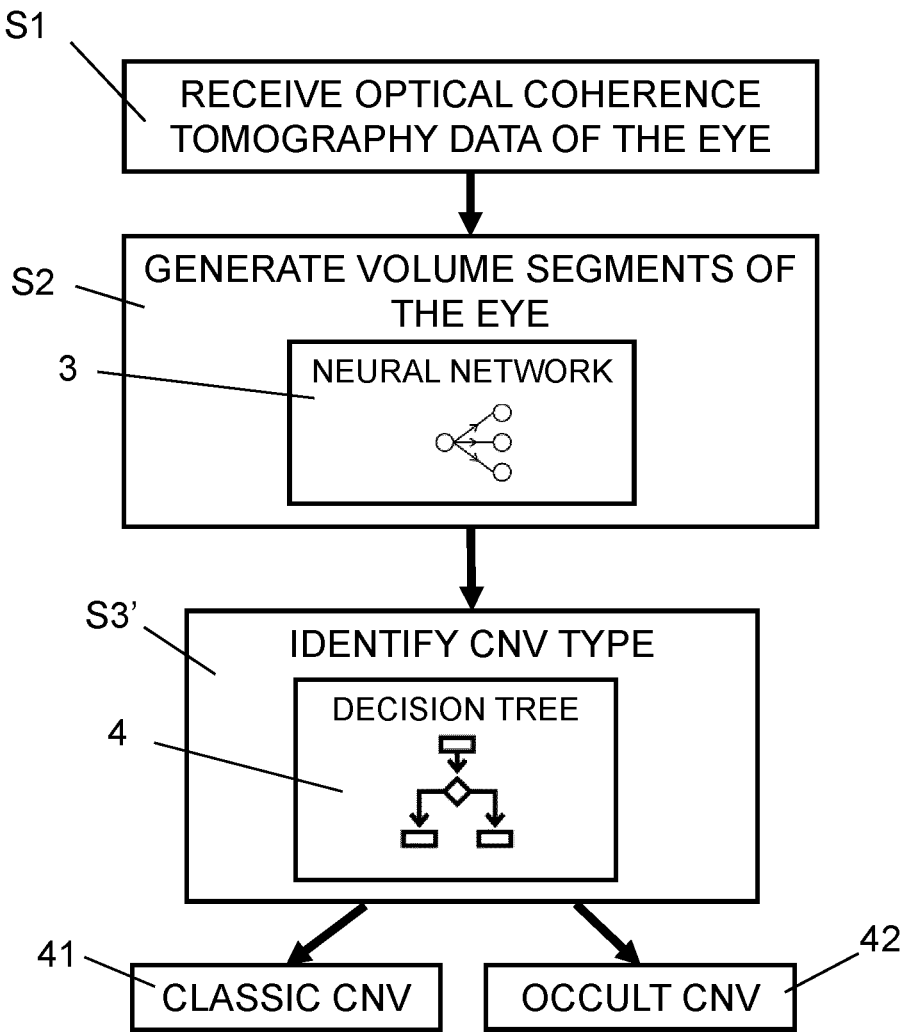
FIG. 6: shows a block diagram illustrating an alternative step for identifying the type of choroidal neovascularization in the eye.

In some non-limiting embodiments, the processor 11 uses a decision tree 4 to identify the type of choroidal neovascularization 40 in the eye, as is explained in more detail in the description of FIG. 6.

In some non-limiting embodiments, the processor 11 also identifies whether any choroidal neovascularization 40 is present at all. The processor 11 can also identify whether both classic choroidal neovascularization 41 and occult choroidal neovascularization 42 are present.

In some non-limiting embodiments, the processor 11 uses the volume segments 2 to identify lesions in the eye. The identified lesions are used by the processor 11 to identify the type of choroidal neovascularization 40.

Figure 3:
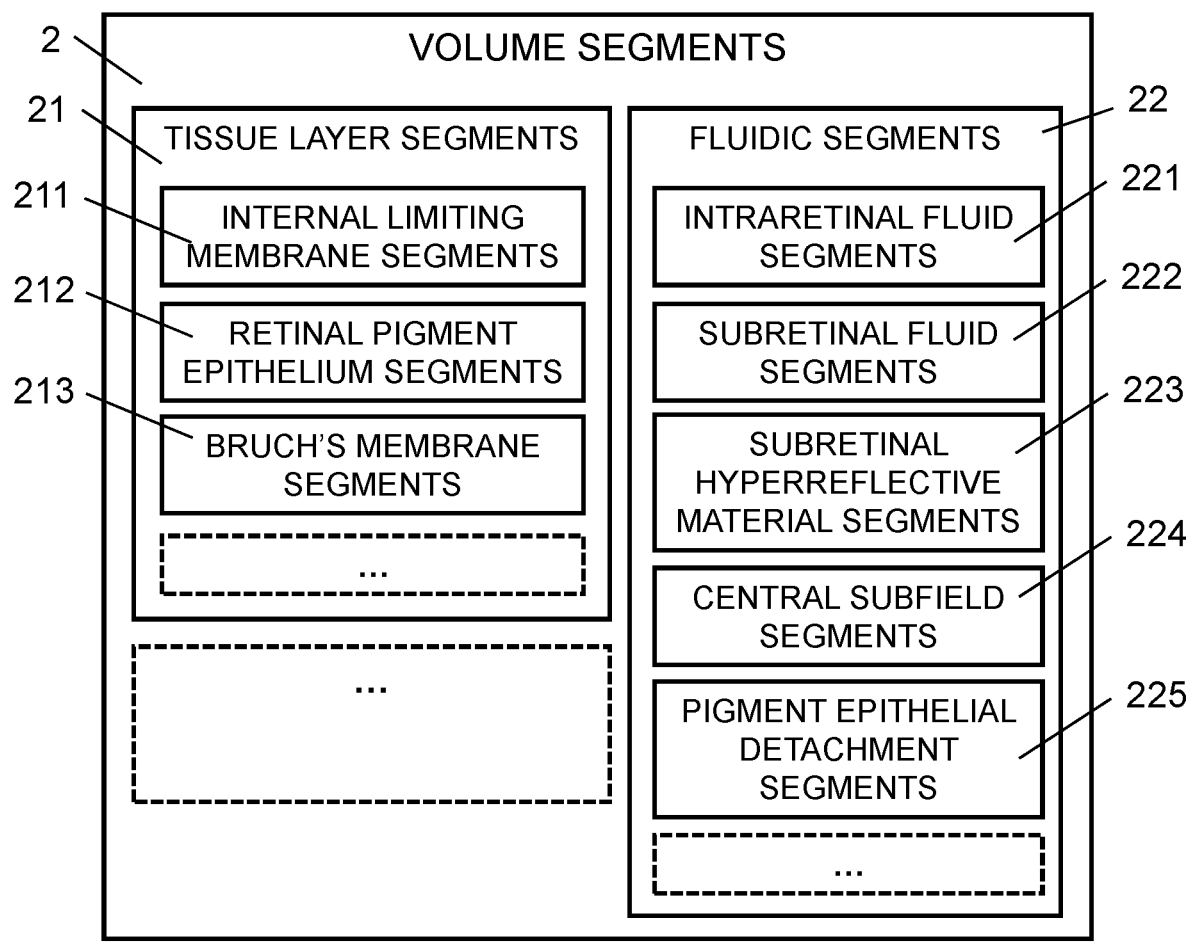
FIG. 3: shows a block diagram illustrating a hierarchy of types of volume segments.

FIG. 3 shows a block diagram illustrating a hierarchy of types of volume segments 2. The volume segments 2 are classified further into tissue layer segments 21 and fluidic segments 22. The tissue layer segments 21 are further classified into at least the following categories: internal limiting membrane segments 211, retinal pigment epithelium segments 212, and Bruch's membrane segments 232. The fluidic segments 22 are further classified into at least the following categories: intraretinal fluid segment 221, subretinal fluid segments 222, subretinal hyperreflective material segments 223, central subfield segments 224, and pigment epithelial detachment segments 225. These listed types of volume segments 2 are not limiting, and other types of volume segments 2 and hierarchies are possible.

In step S2 of FIG. 2, as described above, the processor 11 uses the neural network 3 to generate the volume segments 2 of the eye using the OCT data. Additionally, one or more of the above types of volume segments 2 are assigned by the processor 11, using the neural network, to each generated volume segment 2. In total, when combining the different types of volume segments 2 and the possible features which each volume segment 2 can have associated with it, over 100 features were found to be clinically relevant. These features are either qualitative features, e.g. corresponding to a type of volume segment 2, or are quantitative features, e.g. relating to a position of the volume segment 2 in the eye, or geometric parameters 6 (not shown) of the eye, as is explained in more detail below.

Figure 4:
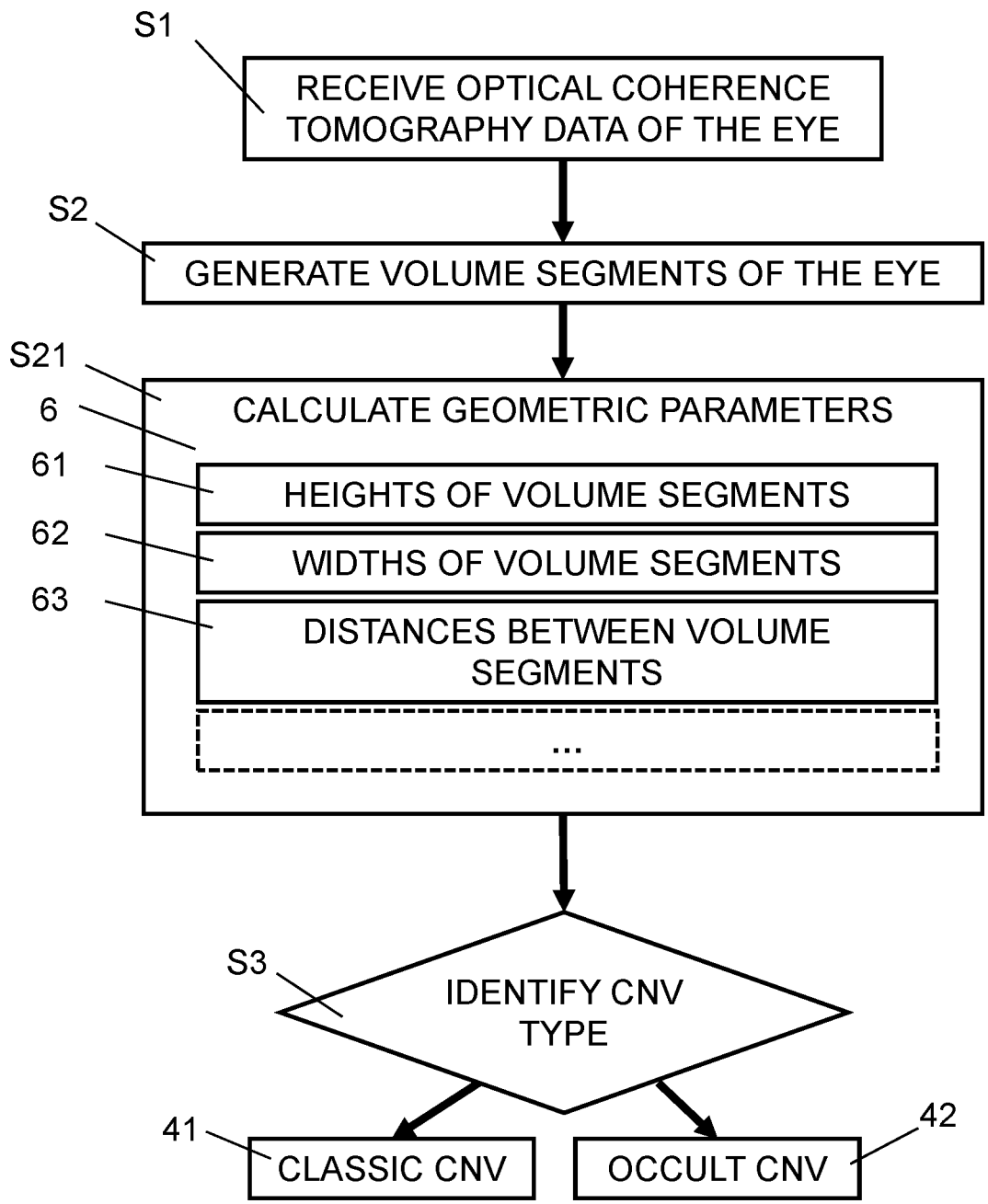
FIG. 4: shows a flow diagram illustrating a sequence of steps for identifying a type of choroidal neovascularization in the eye.

FIG. 4 shows a flow diagram illustrating a sequence of steps for carrying out the invention. An additional step S21 of generating features of the volume segments 2 is shown between step S2 and step S3. In step S21, geometric parameters 6 of the volume segments 2 of the eye are calculated. As described above in the description of FIG. 1, in step S2, the processor 11 uses the neural network 3 to generate volume segments 2 of the eye. The processor 11 then calculates geometric parameters 6 as indicated in step S21. These geometric parameters 6 relate to the volume segments 2 and their size and shape, their location relative to a geometric center of the retina of the eye, and also the spatial arrangement of the volume segments 2 in the retina of the eye. In particular, the geometric parameters 6 comprise one or more from the following list: a height 61 of a given volume segment 2, a width 62 of the given volume segment 2, distances 62 between the given volume segment 2 and other volume segments 2, a volume of the given volume segment 2, a thickness of the given volume segment 2, a measure of how spherical the given volume segment 2 is, and a measure of how smooth the surface of the given volume segment 2 is. These geometric parameters 6 are features assigned to each of the volume segments 2 and used in subsequent steps, in particular in step S3, in which the processor 11 identifies the type of choroidal neovascularization 40 in the eye.

Figure 5:
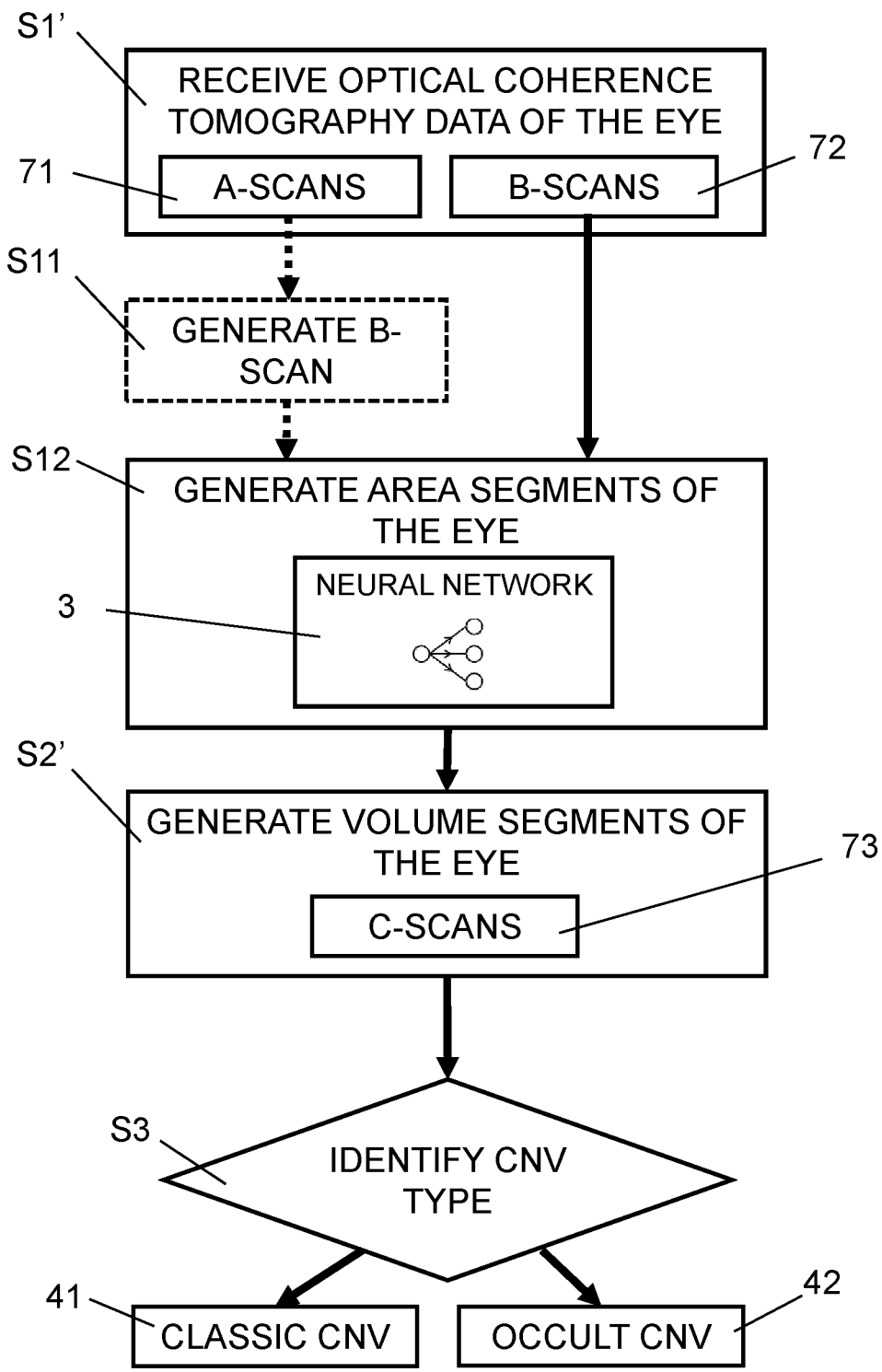
FIG. 5: shows a flow diagram illustrating a sequence of steps for generating volume segments of the eye.

FIG. 5 shows a flow diagram illustrating a sequence of steps for carrying out the invention. In step S1', which is an alternative to step S1 already described above in relation to FIG. 1, the OCT data received by the processor 11 comprises A-scans 71 and/or B-scans 72. In the case that the OCT data received by the processor comprises A-scans 71, the processor 11 combines subsets of the A-scans 71 to generate a sequence of B-scans 72 in the optional step S11. A-scans 71 are one-dimensional scans of the retina of the eye at a given depth. The A-scans are sufficiently dense, both laterally as well as in depth, to allow subsequent high-resolution reconstruction of both two-dimensional cross-sections (B-scans 72) and three-dimensional images of the eye (C-scans 73). If the OCT data comprises B-scans 72, then the processor 11 proceeds directly to step S12.

In step S12 area segments of the two-dimensional B-scans 72 (either received in the OCT data or generated by the processor 11) are generated by the processor 11 using the neural network 3. As B-scans 72 are two-dimensional images, they are well-suited to segmentation by convolutional neural networks, in particular by a neural network 3 comprising a U-Net and/or a ResNet. The U-Net is a convolutional neural network developed for biomedical image segmentation with an architecture designed to yield precise and accurate results with fewer training images than classical fully-connected convolutional neural networks. It achieves this by having, in addition to a contracting part, which detects small features, an up-sampling part which increases the resolution of the output image and which receives contextual information from many of the contracting layers, generating a high resolution output. ResNet is a neural network architecture which uses shortcut, or skip connections, to allow efficient training of deep convolutional neural networks.

In some non-limiting embodiments, the tissue layers present in the B-scans 72 are segmented with a different algorithm than the fluidic layers. Using an algorithm, the following seven tissue layer types of the retina of the eye are segmented into two-dimensional tissue layer segments: Internal Limiting Membrane, Outer Plexiform Layer-Henle's Fiber Layer, Boundary of myoid and ellipsoid inner segments, inner segment/outer segment (IS/OS) Junction, Inner Boundary Retinal Pigment Epithelium, Outer Boundary Retinal Pigment Epithelium, and Bruch's Membrane. Each B-scan 72 and the two-dimensional tissue layer segments in the B-scan 72 generated by the above algorithm is labeled with the appropriate tissue layer type.

In some non-limiting embodiments, the fluidic layers present in the B-scans 72 are segmented into two-dimensional fluidic segments by the processor 11 using the neural network 3 as described above. In particular, the intraretinal fluid, subretinal fluid, subretinal hyperreflective material segments and pigment epithelial detachment layers are detected and labeled in the B-scans 72 and their respective areas defined as two-dimensional fluidic segments.

The generated two-dimensional area segments of successive B-scans 72 are used to generate volume segments 2 of the retina of the eye in step S2. In particular, B-scans 72 comprising two-dimensional fluidic segments and/or two-dimensional tissue layer segments and their respectively assigned features are used by the processor 11 to generate a three-dimensional image (C-scan 73) of the retina of the eye comprising volume segments 2, each segment having an assigned feature according to its type of tissue layer segment or fluidic layer segment. Each pixel of each two-dimensional B-scan 72 either belongs to a two-dimensional area segment, or does not belong to any two-dimensional area segment. If a pixel of a two-dimensional B-scan 72 belongs to a two-dimensional area segment, it is assigned a label according to its type, as enumerated above. Each pixel of a given two-dimensional B-scan is then mapped to a voxel of the C-scan 73 with its given feature. In some non-limiting embodiments, the volume segments 2 are generated such that neighboring volume segments 2 do not contain adjacent fluid layer regions or tissue layer regions of the same type. In particular, the volume segments 2 are generated such that each volume segment 2 corresponds to a single tissue layer segment 2 or a single fluidic segment 22.

FIG. 6 shows a flow diagram illustrating a sequence of steps for carrying out the invention. In step S3', the processor 11 identifies the type of choroidal neovascularization 40 of the eye by using the volume segments 2, the features of the volume segments 2, and a decision tree 4. The decision tree 4 is trained or optimized by using a decision tree training dataset of OCT data of a large number of eyes. The decision tree training dataset comprises volume segments 2 of a large number of eyes along with the type of choroidal neovascularization 40 present in each eye. Preferably, in addition to volume segments 2 of a large number of eyes with choroidal neovascularization, the decision tree training dataset further comprises volume segments 2 of a large number of healthy eyes, i.e. eyes without any type of choroidal neovascularization, as control or reference data. Preferably, the decision tree training dataset comprises data of at least one thousand eyes. Preferably, volume segments 2 of each eye in the decision tree training dataset further comprise associated assigned features which represent a volume segment type along with further descriptors. These features are either categorical, in that they place their associated volume segments 2 into one or more of a given set of categories, or numerical, for example, in that they describe some geometric property of the volume segment 2, such as its volume or extent in a particular direction, as is explained in more detail below.

The processor 11 optimizes the decision tree 4 using the decision tree training dataset, such that the decision tree 4 accurately identifies the type of choroidal neovascularization 40 as defined in the decision tree training dataset. During a particular training iteration, the processor 11 makes a prediction of the type of choroidal neovascularization 40 present in an eye of the decision tree training dataset, and the processor 11 then checks the accuracy of predicted type against the actual type as defined in the decision tree training dataset. The accuracy of the prediction is determined using a logarithmic loss function, and parameters of the decision tree 4 are iteratively optimized to minimize the logarithmic loss function. Preferably, the decision tree 4 is optimized using a gradient boosting algorithm. In an embodiment, an ensemble of decision trees 4 are used with the gradient boosting algorithm. Using a decision tree 4 to identify the type of choroidal neovascularization 40 is advantageous because the decision tree 4 can easily be visualized and comprehended as a flow-chart like structure with transparent and easily understood decision rules. To validate the performance of the decision tree 4 and to ensure that it has not become over-fitted, a separate decision tree validation dataset of at least one hundred eyes previously unseen during training is used. Additionally, cross-validation is used to evaluate the performance by combining the training and validation dataset and then randomly dividing it into a new training dataset and a new validation dataset. After the processor 11 has trained the decision tree 4, the decision tree 4 can additionally be evaluated, and manually tuned or simplified to become more comprehensible, such that the decision tree 4 can deal with edge cases and outliers. The trained decision tree 4 identifies without error whether an eye has choroidal neovascularization or not. The trained decision tree 4 makes it possible to discriminate very well between classic choroidal neovascularization 41 and occult choroidal neovascularization 42, with an area under a receiver operating characteristic curve (AUROC) of 0.91, with the 95% confidence interval being 0.89-0.94.

In an embodiment, the processor 11 uses a CatBoost algorithm to optimize the decision tree 4. The CatBoost algorithm is advantageous because it is robust to over-fitting and because many of the above features are categorical, which the CatBoost algorithm is particularly well suited for.

In an embodiment, the decision tree 4 weights the following types of volume segments 2 the higher than other types of volume segments 2: subretinal hyperreflective material segments, subretinal fluid segments and pigment epithelial detachment segments. In particular, subretinal hyperreflective material segments and pigment epithelial detachment segments are weighted higher than other types of volume segments 2, as they have shown to be the most discriminative characteristics. This means that the presence of volume segments 2, which have a feature of being one of the previously mentioned types of volume segments 2, is more influential in determining the classification of an eye into either classic choroidal neovascularization 41 or occult choroidal neovascularization 42, than other types of volume segments 2. Additional features, such as a size or volume of a given volume segment 2, are also taken into consideration by the decision tree 4.

In some non-limiting embodiments, a plurality of decision trees 4 is used in a random forest model to identify the type of choroidal neovascularization 40. The random forest model is a collection of decision trees whose results are aggregated. The random forest model has the advantage of reducing errors due to bias and errors due to variance.

Figure 7:
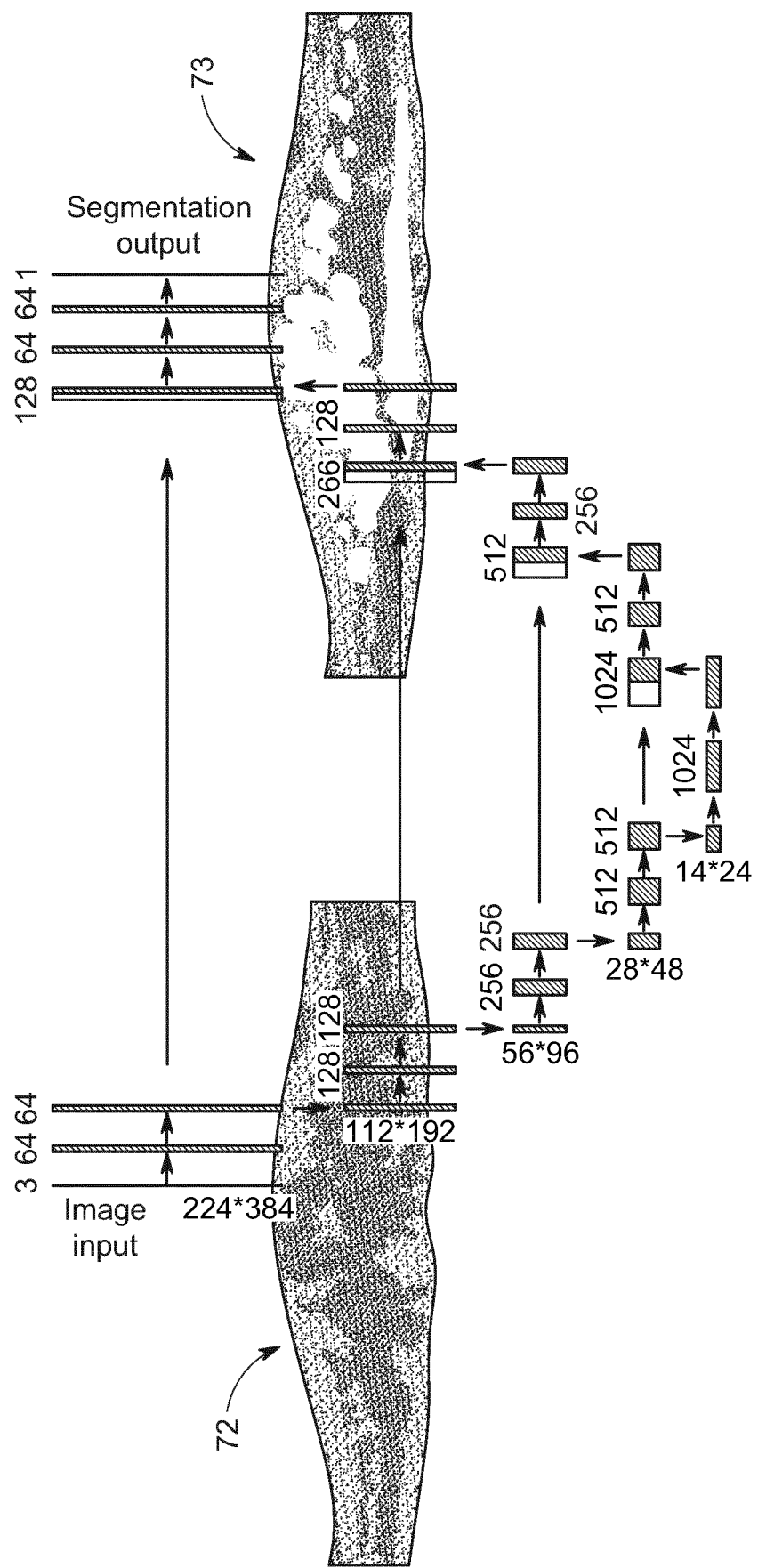
FIG. 7: shows an illustration of a B-scan before and after segmentation.

FIG. 7 shows an illustration of a B-scan 72 (left) and a segmented B-scan 73 (right) with two-dimensional fluidic segments indicated in greyscale. Overlaid on the two images is an illustration of a U-Net used to perform the image segmentation.

Figure 8:
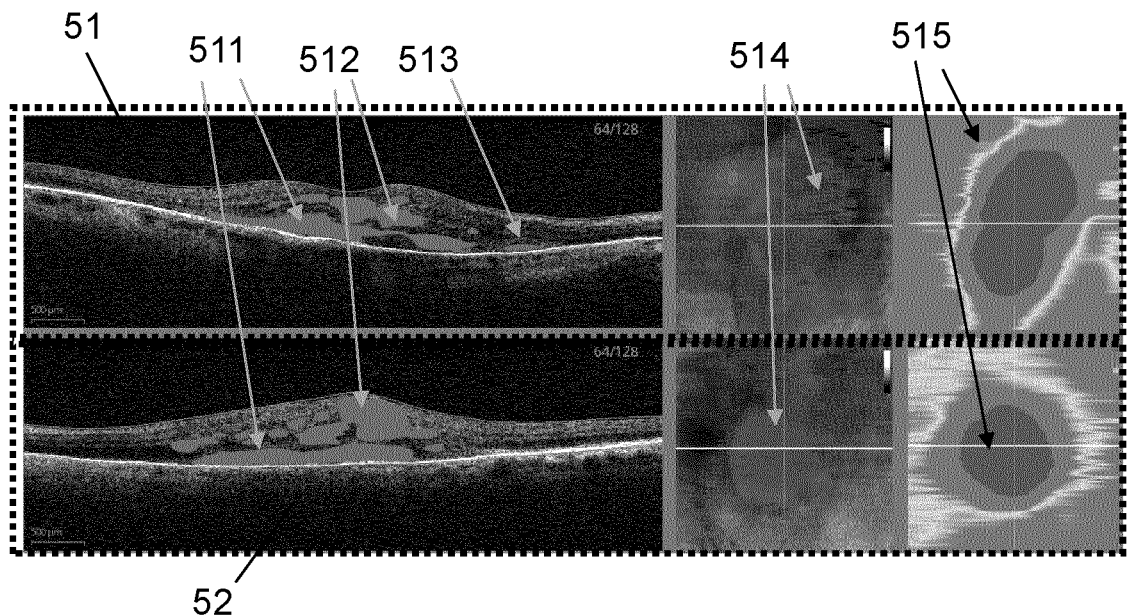
FIG. 8: shows experimental optical coherence tomography data of two eyes featuring classic neovascularization, in particular showing central B-scans with pixel masks for volumetric measures, en face projections, and thickness maps.

FIG. 8 shows two samples, of a retina of an eye 51 (top) showing a typical case of classic choroidal neovascularization 41, and a retina of an eye 52 (bottom), also showing a typical case of classic choroidal neovascularization 41. The B-Scans 72, acquired by SD-OCT, of the respective eyes 51, 52 are on the left, with the fluidic segments of subretinal hyperreflective material 511, intraretinal fluid 512, and subretinal fluid 513 indicated. The middle panels 514 are en face projections of the B-scans and the right-most panels 515 are thickness maps of the respective eyes 51, 52.

Figure 9:
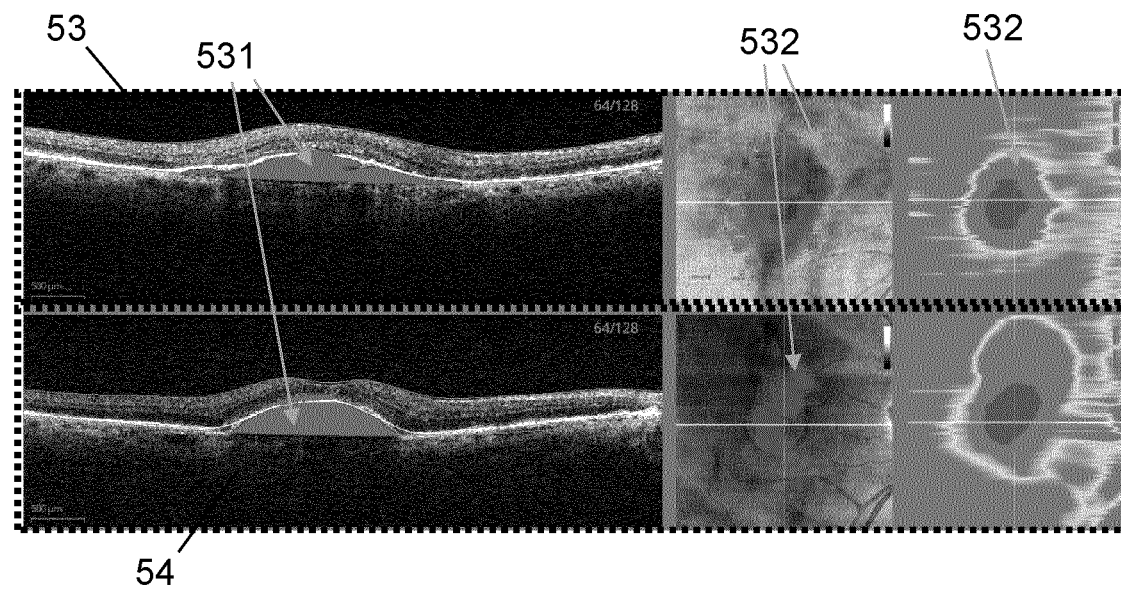
FIG. 9: shows experimental optical coherence tomography data of two eyes featuring occult neovascularization, in particular showing central B-scans with pixel masks for volumetric measures, en face projections, and thickness maps.

FIG. 9 shows two samples of a retina of an eye 53 (top), showing a typical case of occult choroidal neovascularization 42, and a retina of an eye 54 (bottom), also showing a typical case of occult choroidal neovascularization 42. The B-Scans 72, acquired by SD-OCT, of the respective eyes 53, 54 are on the left, with the segments of Pigment Epithelium Detachment 531 indicated. The middle panels 532 are en face projections of the B-scans and the right-most panels 532 are thickness maps of the respective eyes 53, 54.

It should be noted that, in the description, the sequence of the steps has been presented in a specific order; one skilled in the art will understand, however, that the order of at least some of the steps could be altered, without deviating from the scope of the invention.

The invention claimed is:

1. A computer-implemented method for identifying a type of choroidal neovascularization in a human eye, the method comprising:
   receiving, in a processor, optical coherence tomography data of the human eye;
   generating, in the processor, three-dimensional volume segments of the human eye using the optical coherence tomography data and using a neural network, such that at least some tissue layers or fluid layers of a retinal area of the human eye are represented using the three-dimensional volume segments; and
   identifying, in the processor, the type of choroidal neovascularization in the human eye using the three-dimensional volume segments, the type of choroidal neovascularization comprising one or more of the following: classic choroidal neovascularization and occult choroidal neovascularization.

2. The method according to claim 1, wherein generating the three-dimensional volume segments comprises detecting tissue layer segments and fluidic segments.

3. The method according to claim 1, wherein generating the three-dimensional volume segments comprises detecting one or more of the following types of tissue layer segments: internal limiting membrane segments, retinal pigment epithelium segments, and Bruch's membrane segments.

4. The method according to claim 1, wherein generating the three-dimensional volume segments comprises detecting one or more of the following types of fluidic segments: intraretinal fluid segments, subretinal fluid segments, subretinal hyperreflective material segments, central subfield segments, and pigment epithelial detachment segments.

5. The method according to claim 4, wherein identifying the type of choroidal neovascularization comprises weighting the following types of fluidic segments highest: subretinal hyperreflective material segments, subretinal fluid segments and pigment epithelial detachment segments.

6. The method according to claim 1, wherein identifying the type of choroidal neovascularization comprises identifying lesions in the human eye.

7. The method according to claim 1, further comprising:
   calculating one or more of the following geometric parameters: heights of the three-dimensional volume segments, widths of the three-dimensional volume segments, and distances between the three-dimensional volume segments;
   wherein identifying the type of choroidal neovascularization further comprises using the geometric parameters.

8. The method according to claim 1, wherein identifying the type of choroidal neovascularization comprises using a decision tree.

9. The method according to claim 8, wherein identifying the type of choroidal neovascularization comprises optimizing the decision tree using a decision tree training dataset of optical coherence tomography data of a large number of eyes and a gradient boosting algorithm.

10. The method according to claim 1, wherein generating the three-dimensional volume segments comprises training the neural network using machine learning and a neural network training dataset of optical coherence tomography data of a large number of eyes.

11. The method according to claim 1, wherein generating the three-dimensional volume segments using the neural network comprises using a convolutional neural network.

12. The method according to claim 1, further comprising:
   extracting, in the processor, A-scans and/or B-scans from the received optical coherence tomography data;
   wherein generating the three-dimensional volume segments further comprises generating area segments using the A-scans and/or B-scans and the neural network.

13. The method according to claim 1, wherein identifying the type of choroidal neovascularization further comprises identifying whether the human eye has classic choroidal neovascularization, occult choroidal neovascularization, classic choroidal neovascularization and occult choroidal neovascularization, or no choroidal neovascularization.

14. The method of claim 1, wherein the three-dimensional volume segments are generated using the neural network such that each tissue layer or fluid layer of a retinal area of the human eye is represented in a single volume segment.

15. A computer for identifying a type of choroidal neovascularization in a human eye, the computer comprising a processor configured to:

receive optical coherence tomography data of the human eye;

generate three-dimensional volume segments of the human eye using the optical coherence tomography data and using a neural network, such that at least some tissue layers or fluid layers of a retinal area of the human eye are represented using the three-dimensional volume segments; and identify the type of choroidal neovascularization in the human eye using the three-dimensional volume segments, the type of choroidal neovascularization comprising one or more of the following: classic choroidal neovascularization and occult choroidal neovascularization.

16. The computer according to claim 15, wherein generating the three-dimensional volume segments comprises detecting tissue layer segments and fluidic segments.

17. The computer according to claim 15, wherein generating the three-dimensional volume segments comprises detecting one or more of the following types of tissue layer segments: internal limiting membrane segments, retinal pigment epithelium segments, and Bruch's membrane segments.

18. The computer according to claim 15, wherein generating the three-dimensional volume segments comprises detecting one or more of the following types of fluidic segments: intraretinal fluid segments, subretinal fluid segments, subretinal hyperreflective material segments, central subfield segments, and pigment epithelial detachment segments.

19. A computer program product for identifying a type of choroidal neovascularization in a human eye, comprising a non-transitory computer-readable medium having stored thereon computer program code configured to control a processor of a computer to cause the computer to:

receive optical coherence tomography data of the human eye;

generate three-dimensional volume segments of the human eye using the optical coherence tomography data and using a neural network, such that at least some tissue layers or fluid layers of a retinal area of the human eye are represented using the three-dimensional volume segments; and identify the type of choroidal neovascularization in the human eye using the three-dimensional volume segments, the type of choroidal neovascularization comprising one or more of the following: classic choroidal neovascularization and occult choroidal neovascularization.

20. The computer program product according to claim 19, wherein generating the three-dimensional volume segments comprises detecting one or more of the following types of tissue layer segments: internal limiting membrane segments, retinal pigment epithelium segments, and Bruch's membrane segments.

21. The computer program product according to claim 19, wherein generating the three-dimensional volume segments comprises detecting one or more of the following types of fluidic segments: intraretinal fluid segments, subretinal fluid segments, subretinal hyperreflective material segments, central subfield segments, and pigment epithelial detachment segments.

* * * * *